United States Patent [19]

Su et al.

[11] Patent Number: 5,468,643
[45] Date of Patent: Nov. 21, 1995

[54] SWITCHING VALVE SYSTEM FOR DIRECT BIOLOGICAL SAMPLE INJECTION FOR LC ANALYSIS

[75] Inventors: Syang Y. Su, Gaithersburg; Gerald K. Shiu, Laurel, both of Md.

[73] Assignee: The United States of America as represented by the Department of Health and Human Services, Washington, D.C.

[21] Appl. No.: 104,522

[22] Filed: Aug. 10, 1993

Related U.S. Application Data

[63] Continuation of Ser. No. 751,009, Aug. 28, 1991, abandoned.

[51] Int. Cl.$^6$ .................................................. G01N 30/02
[52] U.S. Cl. .................... 436/161; 73/61.55; 210/198.2; 210/656; 422/70; 422/101; 436/177
[58] Field of Search .................................. 422/170, 101, 422/103; 436/161, 177, 178; 210/665, 198.2, 295, 424, 425, 435, 656; 73/23.41, 23.42, 61.56, 61.55, 863.23, 863.24

[56] References Cited

U.S. PATENT DOCUMENTS

| | | | |
|---|---|---|---|
| 3,030,798 | 4/1962 | Lichtenfels | 73/23.42 |
| 3,087,112 | 4/1963 | Pfefferle | 73/23.41 |
| 3,097,519 | 7/1963 | Favre | 73/23.42 |
| 3,206,968 | 9/1965 | Leggoe et al. | 73/23.42 |
| 3,285,701 | 11/1966 | Robertson | 436/161 |
| 3,394,582 | 7/1968 | Munro et al. | 73/23.41 |
| 3,457,787 | 7/1969 | Maatsch et al. | 73/863.24 |
| 3,918,913 | 11/1975 | Stevenson et al. | 422/70 |
| 3,923,460 | 12/1975 | Parrott et al. | 73/61.1 C |
| 4,057,997 | 11/1977 | Chandler | 73/23.41 |
| 4,173,145 | 11/1979 | Durbin | 73/23.41 |
| 4,229,971 | 8/1980 | Ririe, Jr. | 436/177 |
| 4,359,323 | 11/1982 | Le Page | 422/70 |
| 4,446,105 | 5/1984 | Dinsmore et al. | 422/70 |
| 4,454,043 | 6/1984 | Ting et al. | 210/659 |
| 4,526,754 | 7/1985 | Burns et al. | 422/82 |
| 4,577,492 | 3/1986 | Holba et al. | 422/70 |
| 4,751,185 | 6/1988 | Ono et al. | 436/24 |

(List continued on next page.)

OTHER PUBLICATIONS

Perry and Chilton, Chemical Engineer's Handbook, McGraw Hill, New York 1973 pp. 19–57 to 19–81.
Fisher Scientific Catalog 1988 pp. 402–403.
"A New Chromatograph for Pharmacokinetic Drug Monitoring by Direct Injection of Body Fluids", Journal of Chromatography, 222 (1981), pp. 13–22.
94:41093s, Chemical Abstracts, vol. 94, 1981, p. 8.
Single sheet illustrating commercially available embodiments of "Rheodyne Sample Injection Valve".
Single sheet illustrating High Pressure Components, Thomson Instrument Company.

Primary Examiner—James C. Housel
Assistant Examiner—Jan M. Ludlow
Attorney, Agent, or Firm—Lowe, Price, LeBlanc & Becker

[57] ABSTRACT

A valving arrangement and a method are provided by which a biological sample is mixed with a reactant, such as a solvent or a precipitating agent, as it is injected through a multi-position injection valve. A multi-position switching valve is connected to the injection valve, and one or more filters attached to the switching valve remove precipitates of predetermined size from the reacted sample. The sample the flows to conventional analytical columns for liquid chromatography analysis of analytes of interest. Proteins and/or peptides are thus quickly and efficiently removed from the sample as precipitates collected in the filters. The injection valve and the switching valve are then placed in respective cooperating positions to flow a carrier fluid through the injection valve and the switching valve directly to the analysis columns, while a back-flow of a suitable surfactant is pumped through the filters to purge them of collected precipitates. This quickly purges the system and puts it in condition for a repeat of the procedure. The apparatus and method may be used both when samples are provided manually under the direct control of an operator and when an autoinjector or autosampler of known type is employed for repeated sampling.

7 Claims, 2 Drawing Sheets

U.S. PATENT DOCUMENTS

| | | | |
|---|---|---|---|
| 4,837,157 | 6/1989 | Turnell et al. | 436/161 |
| 4,913,821 | 4/1990 | Melcher et al. | 210/635 |
| 4,952,514 | 8/1990 | Haddad | 436/80 |
| 4,980,130 | 12/1990 | Metzger et al. | 422/70 |
| 5,057,437 | 10/1991 | Binder | 436/161 |
| 5,061,638 | 10/1991 | Guter | 436/161 |
| 5,075,080 | 12/1991 | Sanders | 422/70 | ns5,468,643

SWITCHING VALVE SYSTEM FOR DIRECT BIOLOGICAL SAMPLE INJECTION FOR LC ANALYSIS

This application is a continuation of application Ser. No. 07/751,009 filed Aug. 28, 1991, now abandoned.

FIELD OF THE INVENTION

This invention relates to apparatus and methods for performing liquid chromatography analyses on biological samples such as serum, urine, cell and brain tissue, and more particularly to apparatus and a method enabling swift removal of proteins/peptides from samples directly injected into a liquid chromatography system for analysis therein.

BACKGROUND OF THE PRIOR ART

Typically, organic solvent extraction and/or precipitation is utilized to remove various proteins and peptides from sample matrices before liquid chromatography analyses are performed on biological samples of, for example, blood serum, urine, body cells and brain tissue. Such conventional procedures may take between one and six hours and involve tedious and complex steps, including vortexing, centrifuging, drying, and possible reconstitution and repeated drying of the sample material. Because of the numerous steps and extensive handling of the sample material required in such typical processes, contamination of the sample during such handling is not unusual. Consequently, loss of samples poses a serious problem and can result in a low percentage recovery of analytes and a generation of less reproducible test data.

The above-discussed problems can present serious difficulties in validating the results obtained from biological sample analysis. Reproducibility of data is critical for many preclinical and clinical pharmacokinetic studies, hence simplicity that reduces data error or loss is highly desirable both in the apparatus and in the method for handling samples.

Numerous systems and methods for performing liquid chromatography analyses are known. They tend to involve large numbers of cooperating elements and the performance of correspondingly numerous procedural steps.

U.S. Pat. No. 4,751,185 to Ono et al., discloses a method for hop bittering components which comprises a step of separating and analyzing hop bittering components by liquid chromatography. In the disclosed apparatus, a flow line for liquid chromatography and a flow line for pretreatment of a sample are linked by a high pressure switching valve. The polar mobile phase from a supply is introduced into a precolumn which includes an auto injector and is then transferred to a separation column as the flow line is switched over by operation of a high pressure switching valve.

U.S. Pat. No. 4,913,821 to Melcher et al., discloses a method for the determination of phenols in water by adding a halogenating agent to the water, e.g., by employing a bromate-bromide reaction to generate tribromide ions which react with the phenols to form bromo-derivatives of the phenols. The reactive phenol is permeated across a silicone rubber membrane into a liquid extractant such as a solution of sodium hydroxide and acetonitrile. This extractant removes a halogenated derivative of the phenol. The halo-derivative is determined by diverse phase liquid chromatography. The sample and reagent pass to a membrane cell and to an injection valve from a reservoir. By selective positioning of valves in the system, the extractant is passed to the membrane or purged to waste.

U.S. Pat. No. 4,952,514 to Haddad, discloses a method for the analysis of a metal selected from precious metals such as gold, palladium and platinum when these may be present in solution as a cyanide complex, using ion-interaction reverse phase liquid chromatography. In a first washing step, a first eluent is used to coat the surface of a concentrator column with an ion-interaction reagent. This is achieved through the operation of pneumatically actuated low pressure valves, a pump and six-port high pressure switching valves. The valves are all combined and operated in a single automated switching unit.

Other examples of relevant analytical apparatus and methods include U.S. Pat. Nos. 4,577,492 (to Holba et al.), 4,454,043 (to Ting et al.), 3,923,460 (to Parrott et al.), and 4,446,105 (to Dinsmore et al.). Such prior art indicates that the use of a switching valve and one or more other types of valves, including injection valves, is known generally in the art of liquid chromatography.

There is, however, a need for simplified apparatus and a method employing known switching valves, pumps, injection valves and control mechanisms for expeditious and low cost preparation of biological samples for liquid chromatography analyses. This need, as explained more fully hereinbelow, is met by the apparatus and method of the present invention which employs direct injection of biological samples with the use of a switching valve operable in an extremely simple manner to enable quick and low cost liquid chromatography analysis of biological tissue samples.

SUMMARY OF THE INVENTION

It is a principal objective of the present invention to provide apparatus for direct injection of a biological sample into a liquid chromatography system, whereby proteins and/or peptides removed from the biological tissue in the sample are readily filtered and removed from the sample by either direct or programmable automated operation.

It is a related object, according to another aspect of this invention, to provide a method by which a biological sample of a material such as blood serum, urine, cell tissue, brain tissue, or the like, is directly injected into the sample loop of an injection valve in a liquid chromatography system, for quick and effective removal of proteins and/or peptides from the sample material and for subsequent flushing out thereof from the system through either direct or programmable automated operation, with the remaining constituents of the sample conveyed to other equipment for detailed analysis thereof.

These and other related objects of this invention are realized by providing a valving arrangement, for regulating flows in a liquid chromatography (LC) analysis system which includes sources and flow means to provide controlled flows of a sample, a reactant, a carrier fluid to carry the reactant, and a clean-up fluid for cleaning flow passages, wherein a selected constituent of the sample is to be reacted to form removable particulate reaction products to enable analysis of other constituents of the sample by conventional LC equipment, comprising a first valve means, connected to respective sources of a sample, a reactant and a carrier fluid, for providing a first plurality of movable passages which are selectively disposable to receive controlled flows therefrom, said first valve means being provided a sample loop so as to selectively convey at least one of said received flows as an output, and said first plurality of movable passages being movable to a first position so as to selectively direct at least one of said received flows through the sample loop and a second position so as said at least one of said received flows to bypass the sample loop, a second valve means, connected to said first valve means, for providing a second plurality of movable passages which are selectively disposable to receive said output from said first valve means and to convey the received output at a conveyed output, said second valve means being provided with filtering means for filtering particulates of predetermined size from a flow containing particulates, said second plurality of passages being selectively movable to a first position so as to convey said received output through said filtering means and a second position so as to convey the received output to bypass the filtering means, said conveyed output being directed to said conventional LC equipment, said second plurality of passages being connected to a source of clean-up fluid so as to direct a back-flow of clean-up fluid through said filtering means to purge collected particulates therefrom when said received flow is directed to bypass said filtering means.

DESCRIPTION OF THE PREFERRED EMBODIMENTS

In preparing biological samples of materials such as serum, urine, cell tissue or brain tissue for liquid chromatography analysis, one or more selected reactants may be added to the sample material to remove therefrom substances such as proteins or peptides either by dissolving them or by precipitating them from the sample matrix.

Figure 1:
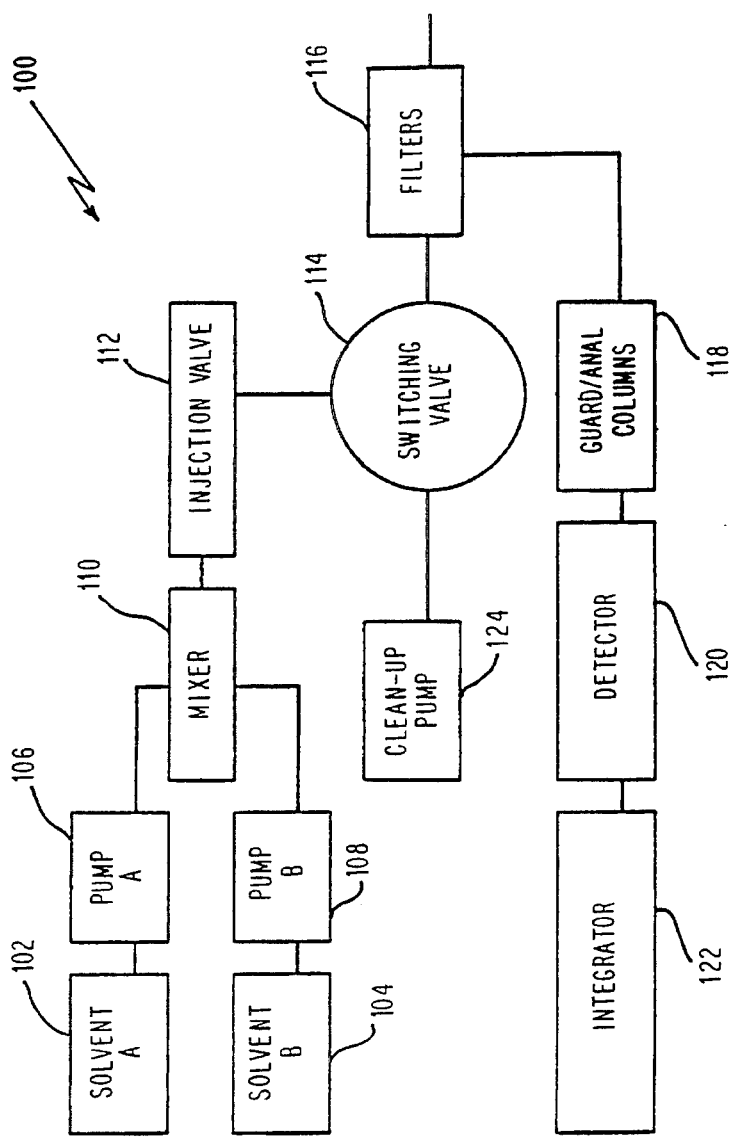
FIG. 1 is a schematic diagram to illustrate the principal cooperating components of a liquid chromatography system, including the apparatus according to a preferred embodiment of this invention.

As illustrated schematically in FIG. 1, in an exemplary system of this general type there may be provided sources 102, 104 of respective reactants A and B, which may be selected to be solvents, precipitating agents or the like as most appropriate. The reactants may be pumped at controlled rates by respective pumps 106 and 108 to a mixer 110 for mixing thereof prior to injecting into the system. Naturally, a single reactant may be used individually by selective operation of the corresponding pump, in which case a mixer would not be needed.

Mixer 110 is connected to an injection valve 112 which may be part of a conventional auto-sampling device or be connected to means for providing a predetermined quantity of a sample material under direct control by a user of the system. Whether the sample is provided in any known way entirely under an operator's direct control or by an auto sampling device, the key is that controlled flows of the sample material and one or more reactants are delivered via a multi-port injection valve 112 to a switching valve 114. The system directs flows, as more fully explained hereinafter, by suitable operations of injection and switching valves 112 and 114.

Figure 2:
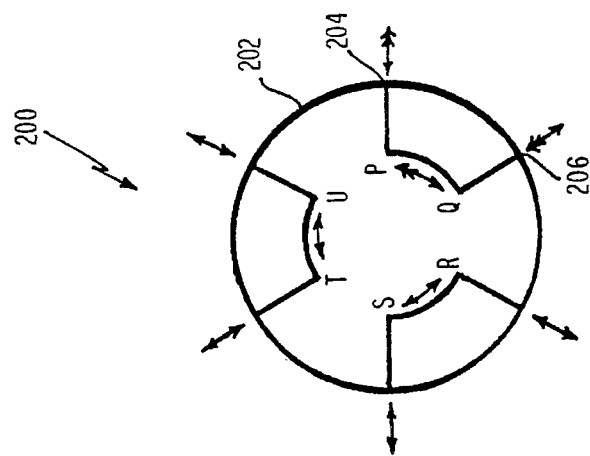
FIG. 2 is a schematic diagram to illustrate flow paths through rotatable core element of an injection valve or a switching valve of a type used in the preferred embodiment.

A number of multi-port, position-adjustable, high and/or low pressure valves are known and commercially available. Typically, such an exemplary valve 200 has an outer body (not shown) that has threaded or otherwise connectable fittings or openings to which various outside lines may be attached, and an internal body 202, formed with one or more passages selectively connectable between these exterior openings to provide predetermined directional flows therethrough, rotatably fitted therein. See FIG. 2, wherein an exemplary passage through rotatable internal body 202 extends from an opening 204 in the direction P to Q and to another opening 206. A flow in this sense or direction would be as pointed out by the single-barbed heads of the double-headed arrows in FIG. 2. Flow in the opposite direction, as would be pointed out by the double-barbed heads of the same double-headed arrows would be in through opening 206 in the direction Q to P and out through opening 204.

Because such elements are very well known, and because the details of their internal structure are not essential to a proper understanding of the present invention, such details will not be discussed further. The key, however, is that by selective rotation of the exemplary multi-passaged internal body 202 of such a valve 200, the flow of a liquid can be correspondingly directed, as described, through appropriate internal passages into selected lines.

A typical commercially available example of such a valve is the Rheodyne (™) valve Model No. 7000.

Like injection valve 112, which has a rotatable internal body 1121 (see FIGS. 3A–3D), switching valve 114 also has a multi-passaged, rotatable internal body 1141 inside a multi-ported outer body (not shown). As more fully explained hereinafter, an important aspect of switching valve 114 is that it is readily fitted with one or more replaceable in-line filters such as 116a and 116b having selected pore-sizes, which may be conveniently mounted to the outer body in any known manner.

Then, as best seen in FIG. 1, flow is directed through one of the ports of switching valve 114 to one or more guard or analysis columns 118 and, thereafter, through one or more detectors such as 120 connected to one or more integrators such as 122. These analytical, detecting and integrating elements may be of any known type and may be operated in known manner. Details of their particular structures are not essential to an understanding of the present invention.

An autoinjector (or autosampler) 126, if one is to be used, may be connected to the injection valve 112, as indicated in FIGS. 3A–3D, for use as described below.

Also connected to one of the ports of switching valve is a clean-up pump 124, and a line 316 to carry away a flow provided thereby to waste. See FIGS. 3A–3D.

What is essential to a realization of the benefits of the present invention is the provision of the multi-ported injection valve 112 with its sample loop and the multi-ported switching valve 114 provided with one or more filters such as 116a and 116b, the same being connected between sources of sample material and the reactants and conventional LC analysis equipment.

Injecting valve 112 and switching valve 114 are operated to work cooperatively with each other and the other elements of the system in successive stages of a sampling/analysis sequence or process to perform their desired operations. This will now be described.

Stage I: Ready to Begin Sampling Procedure

Figure 3A:
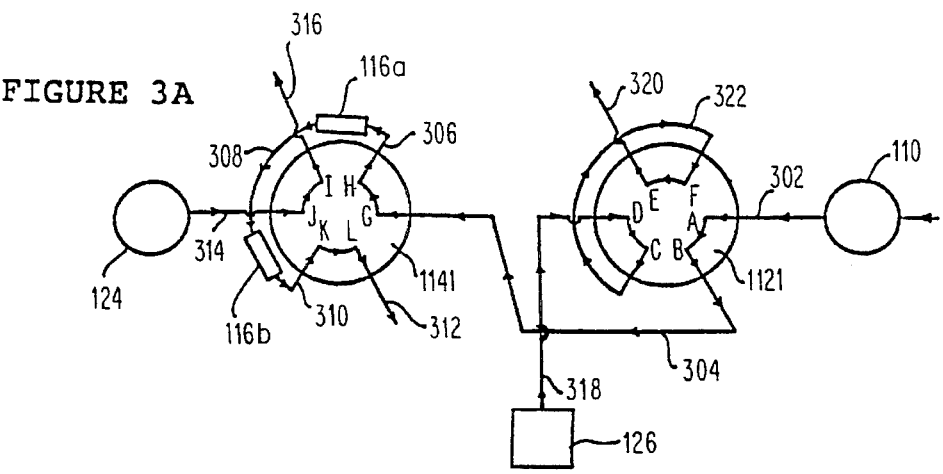
FIGS. 3A–3D are schematic diagrams to illustrate the flow paths of liquids through the cooperating injection valve and switching valve when the valves are disposed in various operational stages of the preferred embodiment of this invention.

FIG. 3A illustrates the disposition of rotatable internal valve bodies 1121 and 1141, which are respectively rotatable within the injection and switching valves 112, 114. Internal valve bodies 1121 and 1141 are thereafter individually and selectively rotated through 60° in the illustrated preferred embodiment in going from one stage to another.

A flow of a reactant, e.g., a precipitating agent, is pumped via mixer 110 into the system at a relatively low flow rate, for example at a rate of 0.2 milliliters per minute, preferably for at least three minutes through line 302 so that the internal passage in valve body 1121 which is identified by the letters A-B is filled with the precipitating agent.

Just before an injection of the reactant takes place, a biological sample of the type described earlier is loaded into sample loop 322, either manually or by an optional autoinjector (or autosampler) 126, via line 318. This biological sample flow takes the path 318-D-C-322-F-E-320, and serves to fill at least the internal passage C-D and sample loop 322 with the sample material. Line 320 can carry any excess flow of sample material to waste.

Stage II: Injection of Reactants to React with Sample Material

Figure 3B:
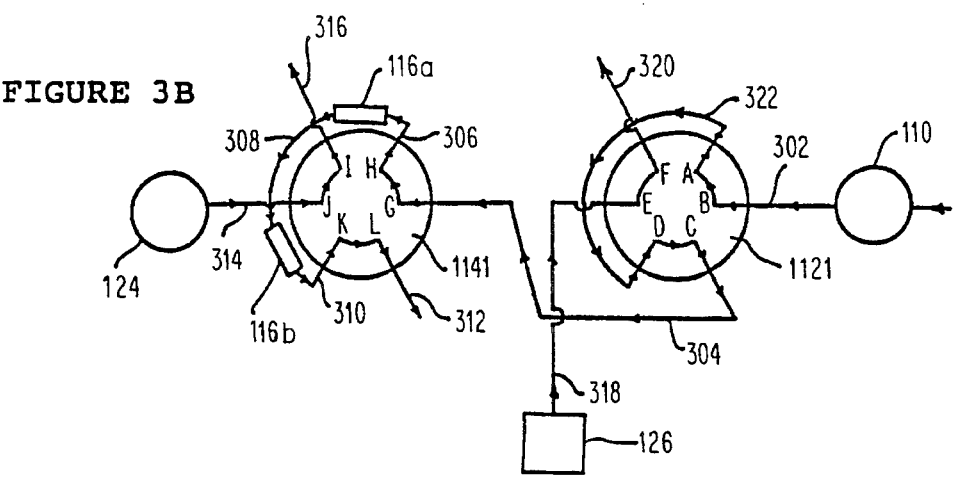

As best understood with reference to FIG. 3B, to put the system into this stage, internal valve body 1121 of injection well 112 is rotated counterclockwise to its position as illustrated.

Note that at the start of this stage the internal passage identified by the letters C-D in internal valve body 1121 of injection valve 112 is already loaded with the biological sample. Sample loop 322 is also filled with the biological sample. A controlled flow of a carrier fluid comprising a reactant material is now started via line 302, and the biological sample contained within the sample loop 322 is pushed therethrough by the flow of reactant material flowing through line 302 and internal passage B-A into sample loop 322.

As this flow continues, there will be continuous mixing between the reactant and the biological sample being pushed out of sample loop 322, thus initiating and continuing a progressive reaction between the reactant and the constituents of the biological sample. This mixing flow passes through internal passage D-C and line 304 to rotatable internal body 1141 of switching valve 114, through internal passage G-H, line 306, a first filter 116a, line 308, optional second filter 116b, line 310, internal passage K-L, and out through line 312 to guard/analytical columns 118.

The rate of flow of the mixing reactant and biological sample is controlled in light of the dimensions of the various internal passages and outside lines so that mixing between the reactant and the constituents of interest in the biological sample is complete before the first filter 116a is reached.

A typical reactant will comprise a precipitating agent selected to react with specific proteins/peptides and will precipitate the products of reaction as particles. Filter 116a is selected to capture relatively large particles precipitated out of the flow. Depending on the pore size of filter 116a, relatively smaller particles will continue their flow therethrough, to be captured by the relatively finer-pored filter 116b. Assorted analytes present in the biological sample but not precipitated and removed therefrom will dissolve in the reactant/precipitating agent and/or carrier fluid being pumped in through the system through mixer 110 and will flow through both the filters and eventually into the guard/analytical column where selected analytes are separated and assessed.

Stage III: Clean-up of Filters, Line and Valve Passages

Figure 3C:
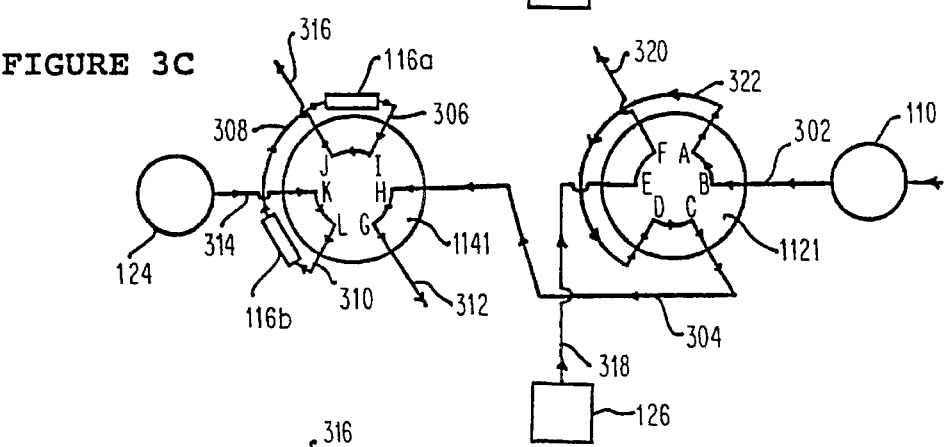

As best understood with reference to FIG. 3C, the rotatable internal body 1141 of switching valve 114 is rotated clockwise, to enable flow from mixer 110 to bypass the filters 116a and 116b so as to enter the guard/analytical columns along the somewhat shorter route: 110-302-B-A-322-D-C-304-H-G-312. In this stage, at between 0.5 and 2 minutes after the start of Stage II in the exemplary operation, the material flowing in through mixer 110, by appropriate operation of pumps 106 and/or 108, may be changed to deliver just a carrier fluid (free of reactant material) through the system containing the injecting valve 112 and switching valve 114 to the guard/analytical columns.

In the meantime, clean-up pump 124 is actuated to flow a clean-up fluid, typically a surfactant solution, through line 314, internal passage K-L of rotatable internal body 1141 of switching valve 114, outside line 310, second filter 116b, line 308, first filter 116a, line 306, internal passage I-J, and out through line 316 to waste. Such a cleaning fluid flow first picks up the small particles trapped in the second filter 116b and carries them through the larger pores of first filter 116a together with any large particles that were captured earlier therein, thus flushing both small and large filtered precipitated particles out of the system. This cleaning flow also cleans out the passages through which it passes and continues until the end of the analysis, and results in specifically cleaning out from both the filters and the internal passages I-J and K-L of switching valve 114 any particulate products of reaction generated by mixing of the reactant and the sample.

Stage IV: Restoration of System to Perform Next Sampling Sequence

Figure 3D:
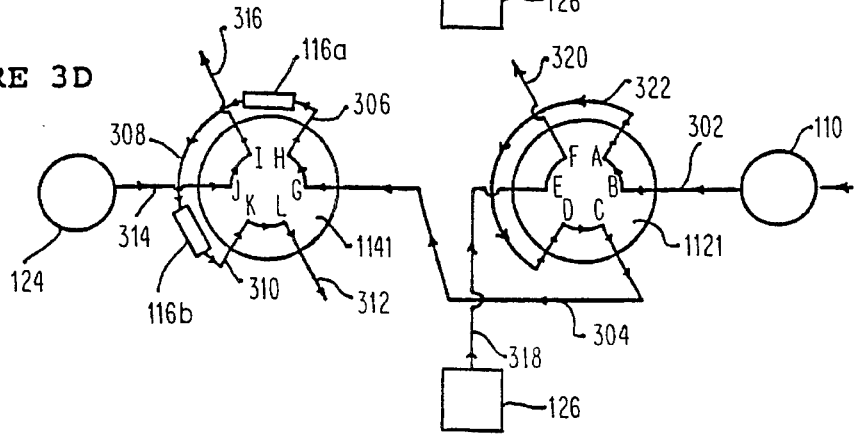

As best understood with reference to FIG. 3D, internal valve body 1141 of switching valve 114 is rotated counterclockwise to its illustrated position. A flow of carrier fluid provided from mixer 110 then takes the following path: 110-B-A-322-D-C-304-G-H-306-116a-308-116a-310-K-L-312-to the guard/analytical columns.

By flowing carrier fluid from mixer 110 in this manner, all of the surfactant solution that was initially flowed through the filters to purge collected particulates therefrom is flushed out of the valve assembly. Again, the rate of flow of carrier fluid in this stage can be readily selected by persons of ordinary skill in the art taking into account the dimensions of the various passages, the type of surfactant fluid used, the dimensions and pore sizes of the filters, and the carrier fluid employed. Such operational parameters are best determined with due account taken of the particular sampling process being conducted with the valving system of the present invention.

In the exemplary sampling process discussed for present purposes, after carrier fluid is thus flowed to purge out any residual refractant solution from the filters and passages G-H and K-L of internal valve body 1141, preferably for between 2 and 5 minutes, the system may be deemed restored to perform the next sampling sequence.

Stage V

As best seen by reference again to FIG. 3A, internal valve body 1121 of the injection valve 112 is rotated clockwise to its original position corresponding to Stage I.

The system is now ready to perform the next sampling procedure.

As will be appreciated from an understanding of the above description, the entire sampling procedure is extremely simple and it involves merely the manipulation of the internal valve bodies of two multi-position valves and some very basic and preprogrammable control over the flows of the sample, the reactant, the carrier fluid and the surfactant.

The entire sampling procedure through all of its described stages can be completed in a matter of mere minutes, and does not require the user to use centrifuges, to collect and transfer the sample and/or fluids to be mixed therewith to other distant or separately located elements, and enables a very compact disposition of the key elements. Laboratory space is usually at a premium in most establishments, and repeated sampling to ensure reproducibility of results may require the performance of a succession of sampling procedures. The present invention, both in its apparatus and in the method of its use, should expedite repeated sampling procedures and because of its simplicity should reduce the overall costs, especially reducing the need for highly-skilled and high-paid technicians.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. A valving arrangement, for regulating flows in a liquid chromatography (LC) analysis system which includes sources and flow means to provide controlled flows of a sample, a reactant, a carrier fluid to carry the reactant, and a clean-up fluid for cleaning flow passages, wherein a selected constituent of the sample is to be reacted to form removable particulate reaction products to enable analysis of other constituents of the sample by LC equipment, comprising:

a first multi-port valve in fluid communication with respective sources of a sample, a reactant and a carrier fluid, for providing a first plurality of movable passages which are selectively disposable to receive controlled flows from each of said sources, said first multi-port valve being provided with a sample loop and said first plurality of movable passages being movable to a first position so as to selectively direct at least one of said received flows through the sample loop and a second position so as to selectively direct at least one of said received flows to bypass the sample loop; and a second multi-port valve in fluid communication with said first multi-port valve for providing a second plurality of movable passages which are selectively disposable to receive a flow output from said first multi-port valve and to convey the received flow output as a conveyed output, said second multi-port valve being provided with filtering means for filtering particulates of predetermined size from a flow containing particulates, said second plurality of passages being selectively movable to a first position so as to convey said received output through said filtering means and a second position so as to convey the received output to bypass the filtering means, said conveyed output being directed to said LC equipment when said second plurality of passages is in each of said first and second positions, said second multi-port valve also being in fluid communication with a source of clean-up fluid so that when said second plurality of passages is in said second position thereof a back-flow of clean-up fluid is directed through said filtering means to purge collected particulates therefrom while said received output is directed to bypass said filtering means.

2. The valving arrangement according to claim 1, further comprising:

sample providing means for providing a predetermined quantity of said sample into said sample loop when said first plurality of passages is disposed in said first position thereof.

3. A valving arrangement according to claim 2, wherein:

said sample providing means comprises autosampler means for repeatedly providing predetermined quantities of sample at predetermined intervals.

4. A valving arrangement according to claim 3, wherein:

said filtering means comprises a plurality of filters connected serially so as to filter out sequentially smaller sized particulates.

5. A method for performing liquid chromatographic analysis using a liquid chromatography (LC) analysis system that includes sources and flow means to provide controlled flows of a sample, a reactant, a carrier fluid to carry the reactant, and a clean-up fluid for cleaning flow passages, wherein a selected constituent of the sample is to be reacted to form the movable particulate reaction products to enable analysis of other constituents of the sample by LC equipment, comprising the steps of:

connecting a first multi-port valve provided with a sample loop and a first plurality of movable passages which are selectively disposable to convey directed flows therethrough to respective sources of a sample, a reactant and a carrier fluid;

connecting a second multi-port valve to said first multi-port valve, said second multi-port valve comprising a second plurality of movable passages which are selectively disposable to receive a flow output from said first multi-port valve and to convey the received output as a conveyed output, said second multi-port valve also being provided with filtering means for filtering particulates of predetermined size from a flow containing particulates;

adjusting said first multi-port valve to a first position and receiving a quantity of a sample to fill at least said sample loop;

adjusting said first multi-port valve to direct a flow of a reactant carried in a carrier fluid through said sample loop to mix with and move the sample contained therein as said flow output flowed to said second multi-port valve;

adjusting said second multi-port valve to a first position to flow said flow output received from said first multi-port valve through said filtering means to remove therefrom precipitated particulate products of a reaction between the reactant and a constituent of the sample; and flowing the filtered flow to said LC equipment for analysis of remaining constituents in the sample.

6. The method according to claim 5, comprising the further steps of:

adjusting said second valve means to dispose said second plurality of passages thereof to direct a backflow of said clean-up fluid to flush collected particulates from said filtering means and to simultaneously direct a flow of a carrier fluid received from said first valve to said LC equipment.

7. The method according to claim 6, comprising the further step of:

adjusting said first valve so as to dispose said first plurality of passages thereof to convey a flow of said carrier fluid through said sample loop and said filtering means to said LC equipment.

* * * * *